United States Patent
Dollyhite et al.

(10) Patent No.: US 7,441,419 B1
(45) Date of Patent: Oct. 28, 2008

(54) THERAPEUTIC COMPRESSION AND CUSHION SOCK AND METHOD OF MAKING

(75) Inventors: Darrell Dollyhite, Rural Hall, NC (US); Rodney Eugene Wilson, Walnut Cove, NC (US); George T. Hicks, Walnut Cove, NC (US)

(73) Assignee: Carolon Company, Rural Hall, CA (US)

( * ) Notice: Subject to any disclaimer, the term of this patent is extended or adjusted under 35 U.S.C. 154(b) by 448 days.

(21) Appl. No.: 11/246,750

(22) Filed: Oct. 7, 2005

(51) Int. Cl.
*D04B 1/26* (2006.01)
(52) U.S. Cl. .................................................. 66/178 A
(58) Field of Classification Search ............... 66/178 A, 66/178 R, 183, 172 E; 2/239, 340
See application file for complete search history.

(56) References Cited

U.S. PATENT DOCUMENTS

| | | | |
|---|---|---|---|
| 4,172,456 A | 10/1979 | Zens | |
| 4,180,065 A * | 12/1979 | Bowen | 602/63 |
| 4,255,949 A * | 3/1981 | Thorneburg | 66/185 |
| 4,397,161 A * | 8/1983 | Chesebro et al. | 66/178 A |
| 4,520,635 A * | 6/1985 | Shields et al. | 66/185 |
| 5,006,401 A | 4/1991 | Frank | |
| 5,307,522 A * | 5/1994 | Throneburg et al. | 2/239 |
| 5,335,517 A * | 8/1994 | Throneburg et al. | 66/185 |
| 6,012,177 A * | 1/2000 | Cortinovis | 2/239 |
| 6,613,007 B1 | 9/2003 | Reid, Jr. | |
| 7,007,517 B2 * | 3/2006 | Menzies | 66/185 |

* cited by examiner

*Primary Examiner*—Danny Worrell
(74) *Attorney, Agent, or Firm*—Kilpatrick Stockton LLP

(57) ABSTRACT

A knitted therapeutic compression and cushion sock and a method for making such a sock include a terry-knit cushioning layer in selected bottom portions of the sock, allowing for greater ventilation and cooling in the top portion. The sock includes graduated zones of compressive pressures. Gradual changes in compressive pressures from one zone of compressive pressure to another can be provided by compression flaring, or changing the feed rate of elasticized yarn during knitting at or near the interface of two zones having different compressive pressures. Such a sock is useful for padding and compressing foot and leg areas to both prevent and treat vascular and skin conditions such as foot and leg ulcers.

17 Claims, 2 Drawing Sheets

THERAPEUTIC COMPRESSION AND CUSHION SOCK AND METHOD OF MAKING

FIELD OF THE INVENTION

The present invention relates to hosiery and, in particular, to socks comprising cushioning and zones of therapeutic compressive pressure construction. Embodiments of the present invention are useful for padding and covering venous ulcers on feet and lower legs.

BACKGROUND OF THE INVENTION

Persons with circulatory and/or skin problems face special challenges with the care and treatment of their feet and lower legs. For example, diabetes can cause reduced circulation and swelling of feet and legs. Such swelling can lead to venous leg ulcers and/or neuropathy with associated reduction or loss of feeling due to nerve damage. Decreased circulation and feeling can contribute to the development of foot sores and infection. Because of such risks and problems related to compromised circulatory and/or skin systems, construction and quality of hosiery is a concern to persons such as those with diabetes. Factors such as cushioning, fit, smoothness, and compression contribute to a hosiery construction aimed at reducing risk of such circulatory, skin, and/or neurological problems.

To address the need for cushioning, conventional socks designed for a person with, or having the potential for, circulatory and/or skin problems in the feet and lower limbs incorporate an increased fabric thickness in the foot area. Another conventional approach to provide enhanced cushioning in a sock is to add cushioning gel materials in the foot area.

A sock that fits poorly or has excessive wrinkles, particularly at anatomical pressure points, can exacerbate circulation, neurological, and/or skin problems, which can lead to further complications, such as skin breakdown, infection, and pain. Conventional sock constructions aimed at improving fit and reducing wrinkles involve designs that are non-binding. For example, a non-binding construction that reduces or prevents "bunching" or tightening of fabric decreases the risk of reduced circulation due to a bind on the foot, toe, ankle, and/or lower leg areas.

Various types of compression hosiery are used to enhance circulation in the lower limbs. However, persons with circulatory problems can develop venous ulcers. Conventional treatment modalities for such ulcers often inhibit use of such compression hosiery. For example, a typical method of treating diabetic-type ulcers of the lower limbs is to apply medication and a dressing over the open wound. The dressing may then be covered with additional padding for protection. One or more layers of stretch bandages are then wrapped around the limb and dressing and any padding to hold the dressing in place and thereby provide a secure environment for the wound. This type of dressing and layers of stretch bandages make the use of standard medical compression hosiery uncomfortable and can even restrict circulation due to tight toe areas, uneven and abrupt compression changes, and bunching or tightening of the fabric.

In addition to the need for designing socks that avoid contributing to circulatory, skin, neurological, and/or other problems associated with, for example, diabetes, there is a need for socks designed to help prevent such problems. Thus, there is a need to provide a sock that improves circulation. There is also a need for a sock that provides a contoured fit, that has smooth transitions from one area of compressive pressure to another. There is also a need for a sock having therapeutic compressive pressures and that provides cushioning in selected areas. Such a sock would reduce the risk of irritation and foot and leg ulcers, can be used to treat such conditions, and would improve the leg and foot health of a person with diabetes.

SUMMARY OF THE INVENTION

The present invention provides embodiments of a sock, and methods for making a sock, comprising therapeutic compressive pressures and an integrally knit cushion layer. In an illustrative embodiment, such a sock can include a base layer comprising an elasticized yarn, a cushion layer integrally knit with the base layer in selected portions on the inside of the sock, and a compressive pressure construction in a plurality of selected circumferential zones. Each of the zones can have the capability of exerting a predetermined amount of compressive pressure on a wearer. For example, each of the zones of compressive pressure construction can have a compressive pressure capability of 20-30 mm Hg, 30-40 mm Hg, or 40-50 mm Hg.

In such a sock, each of at least two zones of compressive pressure construction comprises a different compressive pressure capability. The compressive pressure capability of each of the plurality of zones decreases from a distal portion of the sock to a proximal portion of the sock. In an embodiment, a sock of the present invention can include a transition region between adjacent zones of compressive pressure construction. The elasticized yarn can be knit at a gradually increasing rate of feed in the transition region to provide a gradually decreasing compressive pressure capability in the transition region. Such an embodiment of a sock of the present invention can provide both therapeutic compressive pressures and cushioning support to a wearer.

In an embodiment, the cushion layer can be thicker than the base layer. In another embodiment, the height of the cushion layer can be greater than the height of the base layer. The cushion layer can be knit in selected portions of the sock, for example, around the circumference of the toe portion and on the bottom of the foot and heel portions of the sock. In an alternative embodiment, the cushion layer can be knit around the entire circumference of each portion of the sock. The cushion layer can comprise any knit pattern or construction suitable for providing cushioning to pressure points on the foot of a wearer. For example, the cushion layer can be a terry knit layer.

In an embodiment of the present invention in which the cushion layer is knit on the bottom of, for example, the foot and heel portions of the sock, yarns of the cushion layer can be cut and spliced near the interface between the bottom and the top on each side of the sock. Splicing the ends of the cushion layer yarns at the top/bottom interface helps prevent unraveling of the cut yarns.

In an embodiment, a sock of the present invention can include a heel portion having a "Y" design heel pouch. In another embodiment, a sock of the present invention can include a toe portion having a balloon style construction. A balloon style construction can be accomplished by increasing the number of stitches and/or decreasing the tension on the stitches in the toe portion. In yet another embodiment, a sock of the present invention can include a toe portion having a first toe seam and a second toe seam. The second toe seam can be wider than and sewn over the first toe seam at a height less than the height of the cushion layer so that both toe seams have a relatively low profile for preventing contact stress by the seams.

Embodiments of the present invention include a method of making a therapeutic compression and cushion sock, as described herein.

Features of a therapeutic compression and cushion sock of the present invention may be accomplished singularly, or in combination, in one or more of the embodiments of the present invention. As will be appreciated by those of ordinary skill in the art, the present invention has wide utility in a number of applications as illustrated by the variety of features and advantages discussed below.

A therapeutic compression and cushion sock of the present invention provides numerous advantages over prior hosiery. For example, an embodiment of the present invention can advantageously provide a cushioning layer to selected portions of a sock, for example, to the heel and the bottom portion of the foot, not found in conventional compressive hosiery, that decreases frictional stress to both the heel and foot of a wearer.

Another advantage is that an embodiment of the present invention can provide a cushioning layer on the bottom portion of the foot only so as to allow ventilation and cooling through the top of the foot portion.

Another advantage is that in an embodiment of the present invention, cut yarn ends can be spliced at the interface of the bottom and top portions to prevent unraveling.

Another advantage is that an embodiment of the present invention can provide a therapeutic compression and cushion sock having selected zones of therapeutic compressive pressures to enhance flow in the venous and lymphatic systems.

Another advantage is that an embodiment of the present invention can provide gradual changes in compressive pressure from one area of the sock to another so as to provide smooth transitions between zones of compression. Specifically, an embodiment of the present invention can include compression flaring by changing the rate of yarn feed of elasticized yarn during knitting at or near the interface of two zones having different compressive pressures. Gradual changes in compressive pressures beneficially reduce the risk of a tourniquet effect, impaired circulation, and skin breakdown.

Still another advantage is that an embodiment of the present invention can provide a double toe seam having the same height profile as a knitted terry layer on the inner surface of a sock, thus minimizing stress of the seam line on a wearer's toe area and decreasing the risk of point pressure on the skin of a wearer with compromised circulation and/or skin.

Still another advantage is that an embodiment of the present invention can provide a therapeutic sock that can cover a dressing over an ulcer without the need for additional padding or compressive devices. As such, embodiments of the present invention can provide means for therapeutically padding and compressing a foot and/or lower leg ulcer that has predetermined zones of compressive pressure with gradual changes in different pressures and that is comfortable to a wearer.

Yet another advantage is that an embodiment of the present invention can provide a therapeutic sock that can be worn all day and that reduces edema associated with being on one's feet for prolonged periods, such as standing at a lab bench, work bench, or a manufacturing assembly line, teaching a class, performing surgery, attending to patients, and other jobs requiring prolonged standing.

As will be realized by those of skill in the art, many different embodiments of a therapeutic compression and cushion sock according to the present invention are possible. Additional uses, objects, advantages, and novel features of the invention are set forth in the detailed description that follows and will become more apparent to those skilled in the art upon examination of the following or by practice of the invention.

DETAILED DESCRIPTION

In an embodiment of the present invention, a therapeutic compression and cushion sock can include both cushioning and zones of compressive pressure.

Figure 1:
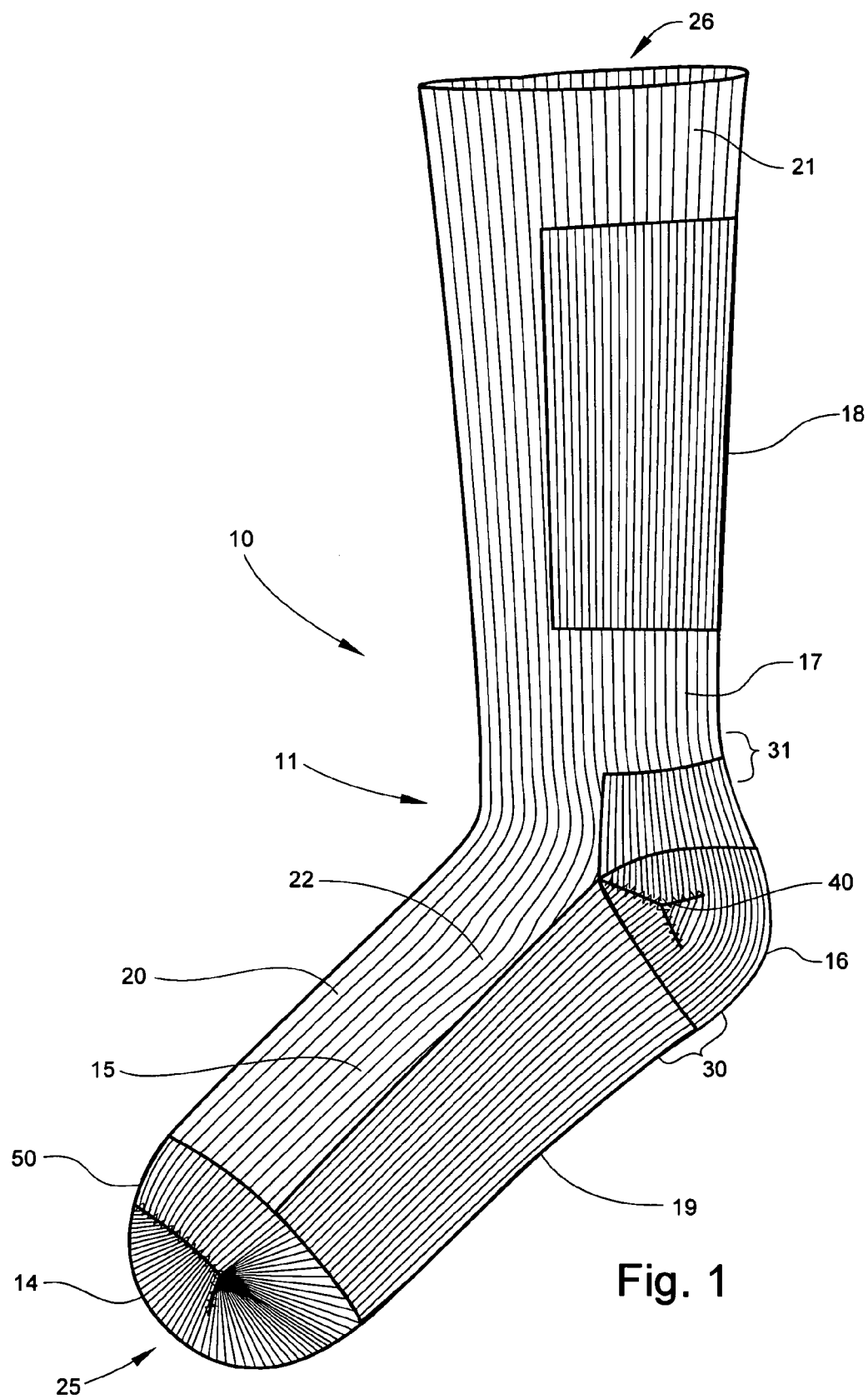
FIG. 1 is a view of the outer surface of a therapeutic compression and cushion sock in an embodiment of the present invention.
Figure 2:
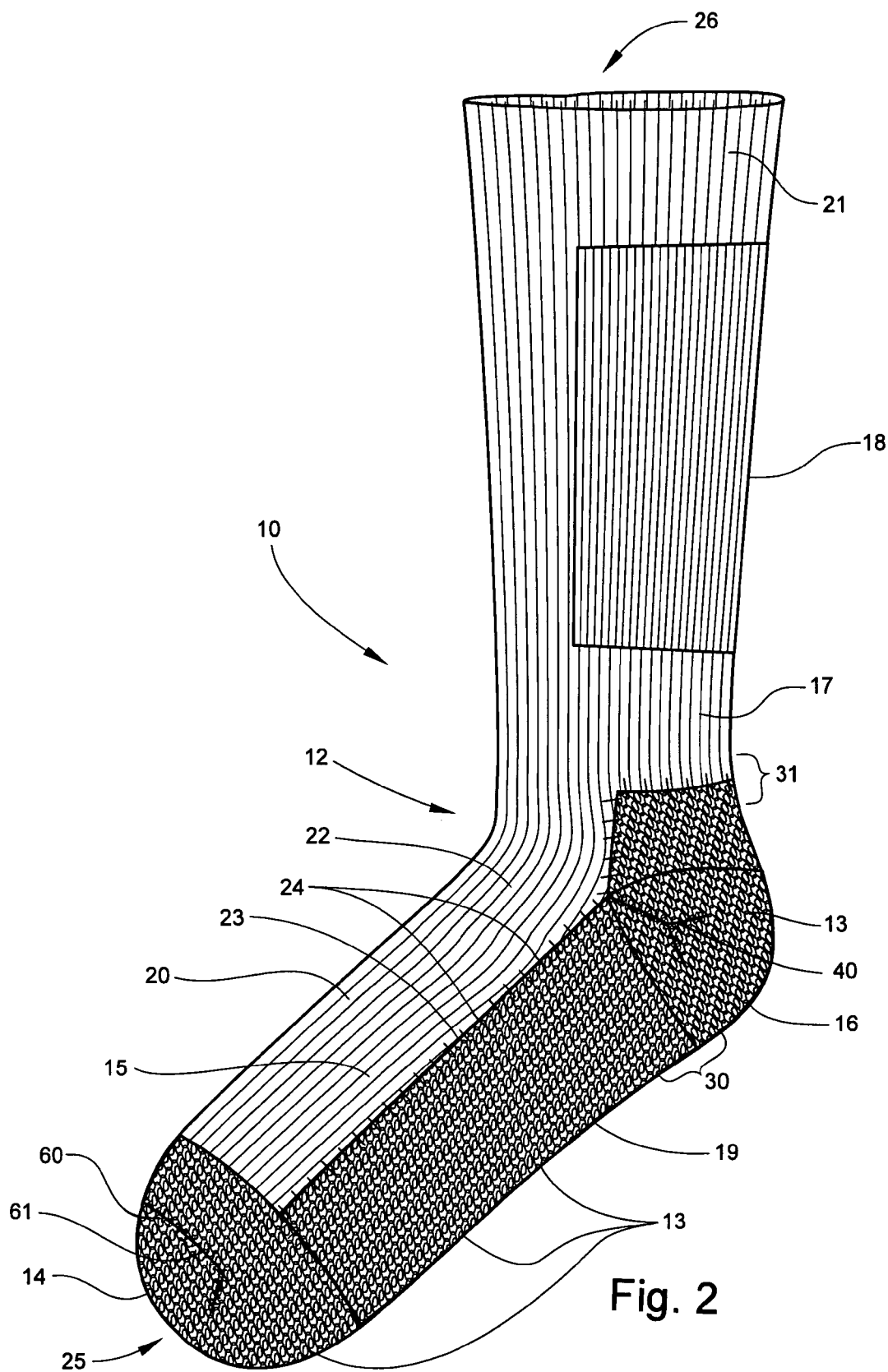
FIG. 2 is a view of the inner surface of a therapeutic compression and cushion sock showing a terry-knit cushion in the toe area and on the bottom of the foot and heel portions in an embodiment of the present invention.

As shown in the embodiment in FIGS. 1 and 2, a therapeutic compression and cushion sock 10 of the present invention comprises a cushion layer 13 in selected areas of the sock 10. FIG. 1 shows the outside 11, and FIG. 2 shows the inside 12 of the sock 10. Portions that can be selected for cushioning include the toe 14, foot 15, heel 16, ankle 17, leg 18, and any combination of these portions. For example, in the embodiment shown in FIGS. 1 and 2, the sock 10 comprises cushioning 13 on the bottom portion 19 of the foot 15 and heel 16 only, thereby providing two layers of fabric in the bottom 19 of the foot portion 15 and in the heel portion 16. In such an embodiment, the top portion 20 of the foot 15 is provided without a cushioning layer 13, thus allowing greater ventilation and more rapid cooling through the top 20 of the foot portion 15 of the sock 10.

In an embodiment, the toe 14, foot 15, and heel 16 portions can be made by circularly knitting yarns including an elasticized yarn as a base layer 21 around the circumference of each portion 14, 15, 16. Base layer 21 yarns can include a double ply yarn. A double ply yarn has two yarns twisted together to form a thicker yarn. Then, a terry cushion layer 13 can be knit on the inside 12 of the sock 10 around the circumference of the toe 14 portion for approximately one inch, or more, from the end of the toe 14, that is, in the so-called "ringtoe" area. The terry cushion layer 13 can also be knit on the bottom portion 19 of the foot 15 and heel 16 portions. A terry cushion fabric 13 is defined as plated fabric knitted with a looped yarn appearing on one side and a ground yarn appearing on the opposite side. To accomplish a terry layer 13 on only the bottom 19 of the foot 15 and heel 16 portions, the terry layer 13 yarns can be cut both at the start of knitting on one side 22 of the foot 15 and heel 16 and at the end of knitting on the opposite side 22 of the foot 15 and heel 16. The loose yarn ends can then be spliced at the interface 23 of the bottom 19 and top 20 portions of the sock 10. Splicing is defined as the process of joining ends of cut yarn by intertwining strands to prevent unraveling. Splices 24 are shown at the interface 23 of the bottom 19 and top 20 of the sock 10 in FIG. 2. In an embodiment of the present invention, cutting the ends of the yarn at the beginning and ending of knitting on the respective sides 22 of the foot 15 and heel 16 portions, rather than completing the courses of knitting around the full circumference of the foot 15 and heel 16, decreases the amount of yarn in the top 20 portion of those portions of the sock 10 and allows the top 20 portion of the foot 15 to have enhanced ventilation and cooling.

In addition to providing protective padding to pad, for example, a foot ulcer, cushioning 13 in the foot 15 and heel 16 portions provides comfort to a wearer of such a sock 10 in areas having a high friction coefficient. Addition of the cushioning layer 13 to the heel 16 and the bottom 19 portion of the foot 15 decreases frictional stress to both the heel and foot of a wearer. An additional cushioning layer 13 also decreases frictional stress to the underlying layer(s) (base layer 21), and increases the useful life of the sock 10.

In another embodiment, a cushioning layer 13, such as a terry knit layer, can be knit around the entire circumference of the sock foot portion 15 to provide a sock 10 with a full foot internal terry cushion. Providing a cushioning layer 13 on the top portion 20 of the foot 15 may be desirable when an ulcer on the top of the foot needs padded protection. In another embodiment, a cushioning layer 13 can be knit only on the top portion 20 of the sock foot portion 15 to provide cushioning on the top 20 of the sock 10 and not on the bottom 19 of the sock 10.

In the present invention, embodiments of a therapeutic compression and cushion sock 10 comprise selected zones of compressive pressure located at the toe 14, foot 15, heel 16, ankle 17, and/or leg 18 areas. These zones can comprise compressive pressures in any medically therapeutic range suitable for application on a foot and/or lower leg of a wearer. For example, an embodiment of a therapeutic compression and cushion sock 10 of the present invention can include therapeutic compressive pressures in one or more areas of a foot and lower leg in the 20-30 mm Hg range (Class I), in the 30-40 mm Hg range (Class II), or in the 40-50 mm Hg range (Class III). Such compressive pressures can be graduated along the length of the sock 10 from the distal portion 25 to the proximal portion 26 so as to enhance flow in the venous and lymphatic systems.

A zone having a compressive pressure construction can include a predetermined compressive pressure capability knit with an elasticized yarn, for example, spandex yarn, having selected characteristics, such as denier value, number of filaments, texturing, and covering with nylon. Zones of compressive pressure can be created by varying the rate of feed of an elasticized yarn and/or the number of stitches including the elasticized yarn in the courses in a particular zone. For example, the selected elasticized yarn can be fed into a knitting dial at a constant rate for a particular compressive pressure. Increasing the rate of feed of the elasticized yarn into the knitting dial decreases the tension on the yarn, resulting in less compressive pressure in that course. Decreasing the rate of feed of the elasticized yarn into the knitting dial increases the tension on the yarn, resulting in more compressive pressure in that course. Likewise, increasing the number of stitches including the elasticized yarn in a course decreases the resulting compressive pressure, and decreasing the number of stitches including the elasticized yarn in a course increases the resulting compressive pressure.

Changes in compressive pressure from one area of the sock 10 to another can be knitted in a gradual fashion so as to provide smooth transitions between zones of compression. Gradual changes in compressive pressure in the sock 10 of the present invention avoids abrupt compression changes to a wearer, thereby reducing the risk of a tourniquet effect, impaired circulation, and skin breakdown.

An embodiment of the present invention can include "yarn flaring," or "compression flaring," to create gradual transitions between zones of compression. Yarn or compression flaring is defined as a gradual change in the rate of yarn feed of elasticized yarn during the knitting of courses at or near the interface of two zones having different compressive pressures. The greater the rate of feed of an elasticized yarn, the less stretched is the yarn, and the lower the compressive pressure in that course. Yarn flaring provides a gradual change in compressive pressures between two zones having different compressive pressures and may not be visibly apparent in the finished sock 10. For example, in an embodiment of the sock 10 of the present invention, the foot portion 15 may comprise a first compressive pressure, the heel portion 16 a second, lower compressive pressure, and the ankle portion 17 a third compressive pressure that is less than the compressive pressures in the foot and heel portions 15, 16, respectively. As the foot portion 15 of the sock 10 is knit, a selected elasticized yarn, for example spandex, is fed into the knitting dial of a circular knitting machine at a predetermined constant rate to create a tubular foot portion 15 having the first compressive pressure. During a predetermined number of courses near the proximal edge of the foot portion 15, as a transition begins toward the heel portion 16, the rate of feed of the elasticized yarn into the knitting dial is gradually increased. The gradual increase in rate of elasticized yarn feed continues for a predetermined number of courses into the heel portion 16 until a constant yarn feed rate is reached to achieve the predetermined second compressive pressure in the heel portion 16. The increase in rate of elasticized yarn feed causes the elasticized yarn to be knit in a less stretched manner, resulting in a gradually less compressive pressure in the tubular foot-to-heel transition region 30.

After the heel portion 16 is knit with the constant yarn feed rate to achieve the predetermined second compressive pressure, a transition region 31 between the heel portion 16 and the ankle portion 17 is knit. The heel-to-ankle transition region 31 can extend from a predetermined number of courses of yarn in the heel portion 16 through the a predetermined number of courses of yarn in the ankle portion 17. In this heel-to-ankle transition region 31, the rate of feed of the elasticized yarn into the knitting dial is gradually increased. The gradual increase in rate of elasticized yarn feed continues into the ankle portion 17 until a constant yarn feed rate is reached to achieve the predetermined third compressive pressure in the ankle portion 17. The increase in rate of elasticized yarn feed causes the elasticized yarn to be knit in a less stretched manner, resulting in a gradually less compressive pressure in the heel-to-ankle transition region 17.

In an embodiment, yarn or compression flaring can occur gradually at the end of one portion and at the beginning of the adjacent portion of the sock 10, for example over a one inch or more region. A yarn or compression flaring region can occur between any two adjacent zones having different compressive pressures. For example, in addition to a foot-to-heel transition region 30 and a heel-to-ankle transition region 31, yarn or compression flaring can be present in an ankle-to-leg transition region or other transition region.

Compression flaring results in gradual changes in compressive pressure from one portion of the sock 10 to another such that smooth transitions are provided between zones having different compressive pressures. Such smooth transitions in compressive pressure in the sock 10 of the present invention prevent abrupt compression changes that may cause skin irritation and/or a tourniquet effect to a wearer. As a result, the risk of impaired circulation and skin breakdown related to use of a sock having varying compressive pressures is reduced.

An embodiment of the therapeutic compression and cushion sock 10 of the present invention can include a heel pouch 40 having a "Y" design to provide a deeper pocket for a better fit. The heel pouch 40 is knitted with extra courses of yarn to accommodate the heel of a wearer. In a standard heel, half of the knitting needles knit in the heel section 16, with narrowing occurring at each side, until only one-third of the needles are left in action. As each needle is lifted out of action, the yarn is automatically wrapped over it in the form of a tuck stitch, which makes the heel join stronger. Widening then takes place until all heel section needles are brought back into operation, when circular knitting recommences. In the "Y" design heel pouch 40, the heel 16 is knit by narrowing to less than all of the knitting needles, for example one-third of the needles. Then, extra yarn is knitted in the center of an inverted "Y" suture-line by widening for a predetermined number of courses, for example twelve courses. Narrowing then occurs again by knitting on less than all of the knitting needles (one third of the needles, for example), after which widening and then circular knitting occurs.

In an embodiment, the sock 10 can include a "balloon style" toe portion 50 that provides for pressure relief in the toe area 14. A "balloon style" toe portion 50 can be accomplished by increasing the number of stitches in the toe portion 14 or by decreasing the tension on the stitches in the toe portion 14.

As described herein, an embodiment of the sock 10 of the present invention can include both the cushioning layer 13 and one or more zones of therapeutic compressive pressure. Conventional dressings for leg and foot ulcers are wrapped with padding and one or more layers of elastic bandages. An embodiment of the sock 10 of the present invention can cover a dressing over a wound, for example, a venous stasis ulcer, without the need for additional padding or compressive devices. As such, the present invention provides means for therapeutically padding and compressing a foot and/or lower leg wound or ulcer that has predetermined zones of compressive pressure with gradual changes between different pressures and that is comfortable to a wearer.

In an embodiment of the present invention, the therapeutic compression and cushion sock 10 can include a double toe seam having the same or lower profile, or height, as the knitted terry cushion layer 13 on the inside 12 of the sock 10. A low profile, double toe seam can be accomplished by first cutting away excess fabric at the toe opening using conventional techniques on a toe seaming machine. In such an embodiment, a first seaming needle and looper on the toe seaming machine are set to stitch through only the courses of fabric at the edge of the toe opening to form a narrow first toe seam 60 and thereby close the toe opening. A second seaming needle assembly can be set to then stitch a second, wider toe seam 61 over the top of the first seam 60, which causes the first seam 60 to lie tighter and flatter against the inside 12 surface of the sock 10. The second "over-cast" toe seam 61 provides a seam line that is lower than, or that approximates the height of, the surrounding terry cushion layer 13 from the inside 12 surface of the sock 10, thus minimizing stress of the seam line on a wearer's toe area. Such a low profile toe seam decreases the risk of point pressure on the skin of a wearer with compromised circulation and/or skin and provides a smoother, more comfortable fit of the sock 10.

In the present invention, embodiments of the sock 10 can comprise a variety of yarns suitable for use in regular fashion socks as well as yarns usable in therapeutic compression hosiery. In one illustrative embodiment, yarns of the sock 10 can comprise 66% nylon, 20% cotton, and 14% spandex. Cotton yarns utilized in the terry-knit cushion layer 13 can be combed cotton yarns or a pima cotton. Combed cotton yarn is a cotton yarn that has been combed into a more even, compact yarn having fewer projecting fibers. In an embodiment, an elasticized yarn can be a spandex yarn having a denier of 560 and can be double covered with 270/34 nylon. Spandex is defined as a manufactured fiber in which the fiber-forming substance is a long-chain synthetic polymer comprises at least 85% segmented polyurethane. Denier is defined as a measure of the density of a manufactured fiber, numerically equivalent to the number of grams per 9,000 meters length of the fiber. The larger the denier number, the denser the fiber. Nylon yarn is identified by nomenclature in which the denier of the yarn is noted first, followed by the number of filaments in the yarn. For example, a "270/34" nylon comprises a nylon yarn having 34 filament of 270 denier each. Socks of the present invention can be made in various lengths, including thigh, knee, over-the-calf, and ankle lengths. Socks of the present invention can also include sizing marks to ensure proper identification and packaging.

In a method of making the sock 10 according to the present invention, the base layer 21 is knit with yarns including an elasticized yarn. A terry knit cushion layer 13 can be knit with the base layer 21 in selected portions on the inside 12 of the sock 10 to provide a means for cushioning areas of a wearer's foot and/or leg corresponding to the selected portions of the sock 10 having the cushion layer 13. A construction capable of exerting a predetermined amount of compressive pressure on a wearer can be knit in a plurality of selected circumferential zones in the sock 10. In an embodiment of a method, at least two zones of compressive pressure construction, each zone having a different compressive pressure capability can be knit. Zones of compressive pressure capability can be knit such that compressive pressure capability decreases from the distal 25 toe portion 14 to the proximal 26 leg 18 or top portion of the sock.

The sock 10 of the present invention made by such a method can include a transition region, for example, foot-to-heel transition region 30 and heel-to-ankle transition region 31, between adjacent zones of compressive pressure construction. In the transition regions 30, 31, the rate of feed of the elasticized yarn is gradually increased to provide a gradually decreasing compressive pressure capability in the transition regions 30, 31. For example, the elasticized yarn can be knit at a first constant feed rate in a first zone, for example, in the foot 15, to provide a first compressive pressure capability. In the transition region 30 from the first zone to an adjacent second zone, for example, the heel 16, the elasticized yarn can be knit at a gradually increasing feed rate until a second constant feed rate is achieved. This change in feed rate of the elasticized yarn provides a gradually decreasing compressive pressure capability in the transition region 30. The elasticized yarn can then be knit at the second constant feed rate, which is greater than the first constant feed rate, to provide a second zone (in the heel 16) having a second compressive pressure capability less than the first compressive pressure capability.

An embodiment of a method of the present invention can further include cutting and splicing yarns of the cushion layer 13 at or near the interface 23 of the bottom 19 and top 20 on each side 22 of the sock 10. An embodiment of a method can further include knitting a heel pouch 40 in a "Y" design. In another embodiment of a method, the toe portion 14 of the sock 10 can be knit with an increased number of stitches and/or with a decreased tension on the stitches to provide a balloon construction 50 for relieving pressure on the toes of a wearer. In another embodiment of a method, the toe portion 14 opening can be sewn with a narrow first toe seam 60, and then sewn with a second toe seam 61 wider than and overlying the first toe seam 60 so that both the first and second toe seams 60, 61, respectively, have a height no greater than the height of the cushion layer 13.

Although the present invention has been described with reference to particular embodiments, it should be recognized that these embodiments are merely illustrative of the principles of the present invention. Those of ordinary skill in the art will appreciate that a therapeutic compression and cushion sock of the present invention may be constructed and utilized in other ways and embodiments. Accordingly, the description herein should not be read as limiting the present invention, as other embodiments also fall within the scope of the present invention.

What is claimed is:

1. A sock, comprising:
a base layer comprising an elasticized yarn;
a cushion layer integrally knit with the base layer in selected portions on an inside of the sock;
a compressive pressure construction in a plurality of selected circumferential zones of the sock, each of the zones capable of exerting a predetermined amount of compressive pressure on a wearer,
wherein each of at least two zones of compressive pressure construction comprises a different compressive pressure capability,
wherein the compressive pressure capability of each of the plurality of zones decreases from a distal portion of the sock to a proximal portion of the sock; and
a transition region between adjacent zones of compressive pressure construction, wherein the elasticized yarn is knit at a gradually increasing rate of feed to provide a gradually decreasing compressive pressure capability in the transition region.

2. The sock of claim 1, wherein the cushion layer comprises a thickness greater than a thickness of the base layer.

3. The sock of claim 1, further comprising toe, foot, and heel portions, wherein the cushion layer is knit around a circumference of the toe portion and on a bottom of the foot and heel portions of the sock.

4. The sock of claim 1, wherein the cushion layer is knit around a circumference of each portion of the sock.

5. The sock of claim 1, wherein the cushion layer comprises a terry knit cushion layer.

6. The sock of claim 1, further comprising a bottom, a top, and two sides, wherein yarns of the cushion layer are cut and spliced near an interface of the bottom and the top on each side of the sock.

7. The sock of claim 1, wherein each of the zones of compressive pressure construction comprises a compressive pressure capability of 20-30 mm Hg, 30-40 mm Hg, or 40-50 mmHg.

8. The sock of claim 1, further comprising a heel portion, wherein the heel portion comprises a "Y" design heel pouch.

9. The sock of claim 1, further comprising a toe portion having a balloon style construction, wherein the balloon style construction comprises an increased number of stitches or a decreased tension on the stitches.

10. A sock comprising:
a base layer comprising an elasticized yarn;
a cushion layer integrally knit with the base layer in selected portions on an inside of the sock;
a compressive pressure construction in a plurality of selected circumferential zones of the sock, each of the zones capable of exerting a predetermined amount of compressive pressure on a wearer; and
a toe portion having a first toe seam and a second toe seam wider than and sewn over the first toe seam at a height less than a height of the cushion layer.

11. A sock, comprising:
a toe portion, a heel portion, a bottom, a top, and two sides;
a base layer comprising an elasticized yarn;
a terry knit cushion layer integrally knit with the base layer in selected portions on an inside of the sock;
a compressive pressure construction in a plurality of selected circumferential zones of the sock, each of the zones capable of exerting a predetermined amount of compressive pressure on a wearer;
each of at least two zones of compressive pressure construction comprising a different compressive pressure capability;
the compressive pressure capability of each of the plurality of zones decreasing from a distal portion of the sock to a proximal portion of the sock; and
a transition region between adjacent zones of compressive pressure construction,
wherein in the transition region the elasticized yarn is knit at a gradually increasing rate of feed to provide a gradually decreasing compressive pressure capability in the transition region,
wherein yarns of the cushion layer are cut and spliced near an interface of the bottom and the top on each side of the sock,
wherein the heel portion comprises a "Y" design heel pouch,
wherein the toe portion comprises a balloon style construction, the balloon style construction comprising an increased number of stitches or a decreased tension on the stitches, and
wherein the toe portion comprises a first toe seam and a second toe seam wider than and sewn over the first toe seam at a height less than a height of the cushion layer.

12. A method of making a sock, comprising:
knitting at least an elasticized yarn into a base layer;
integrally knitting a terry knit cushion layer with the base layer in selected portions on an inside of the sock;
knitting a plurality of zones of compressive pressure construction, each of which zones comprises a different compressive pressure capability capable of exerting a predetermined amount of compressive pressure on a wearer;
knitting a decreasing compressive pressure capability of each of the plurality of zones from a distal portion of the sock to a proximal portion of the sock; and
knitting a transition region between adjacent zones of compressive pressure construction by gadually increasing a rate of feed of the elasticized yarn to provide a gradually decreasing compressive pressure capability in the transition region.

13. A method of making a sock, comprising:
knitting at least an elasticized yarn into a base layer;
integrally knitting a terry knit cushion layer with the base layer in selected portions on an inside of the sock; and
knitting in a plurality of selected circumferential zones in the sock a construction capable of exerting a predetermined amount of compressive pressure on a wearer,
wherein knitting a compressive pressure construction further comprises
knitting the elasticized yarn at a first constant feed rate in a first zone to provide a first compressive pressure capability;
knitting the elasticized yarn at a gradually increasing feed rate until a second constant feed rate is achieved to provide a transition region between the first zone and an adjacent second zone, the transition region having a gradually decreasing compressive pressure capability; and
knitting the elasticized yarn at the second constant feed rate greater than the first constant feed rate in the second zone to provide a second compressive pressure capability less than the first compressive pressure capability.

14. The method of claim 12, further comprising cutting and splicing yarns of the cushion layer near an interface of a bottom and a top on each side of the sock.

15. The method of claim 12, further comprising knitting a heel pouch in a "Y" design.

16. The method of claim 12, further comprising knitting an increased number of stitches in a toe portion of the sock or knitting the toe portion with a decreased tension on the stitches.

17. A method of making a sock, comprising:
- knitting at least an elasticized yarn into a base layer;
- integrally knitting a terry knit cushion layer with the base layer in selected portions on an inside of the sock;
- knitting in a plurality of selected circumferential zones in the sock a construction capable of exerting a predetermined amount of compressive pressure on a wearer; and
- sewing a first toe seam, and sewing a second toe seam wider than and overlying the first toe seam so that both the first and second toe seams have a height no greater than a height of the cushion layer.

\* \* \* \* \*